United States Patent [19]

Duvvuri et al.

[11] Patent Number: 5,763,477
[45] Date of Patent: Jun. 9, 1998

[54] TAXANE DERIVATIVES FROM 14-β-HYDROXY-10 DEACETYLBACCATIN III

[75] Inventors: Subrahmanyam Duvvuri; Venkateswarlu Akella; Sharma Manohar Vedula; Ramachandra Puranik; Raghavendra Madhva Sattegeri, all of Miyapur, India

[73] Assignee: Dr. Reddy's Research Foundation, Hyderabad, India

[21] Appl. No.: 471,639

[22] Filed: Jun. 6, 1995

[30] Foreign Application Priority Data

| Jul. 22, 1994 | [IN] | India | 681/94 |
| Jul. 22, 1994 | [IN] | India | 682/94 |
| Jul. 22, 1994 | [IN] | India | 683/94 |
| Jul. 22, 1994 | [IN] | India | 684/94 |
| Jul. 22, 1994 | [IN] | India | 685/94 |

[51] Int. Cl.$^6$ .................. A61K 21/335; C07D 321/10
[52] U.S. Cl. ............................. 514/450; 549/348
[58] Field of Search ................ 549/348; 514/450

[56] References Cited

U.S. PATENT DOCUMENTS

| 5,264,591 | 11/1993 | Bombardelli et al. ............ 549/214 |
| 5,635,531 | 6/1997 | Chen ................................... 514/471 |

FOREIGN PATENT DOCUMENTS

| 0559019 | 9/1993 | European Pat. Off. |
| 9321173 | 10/1993 | WIPO |
| 94/22856 | 10/1994 | WIPO |
| 96/30373 | 10/1996 | WIPO |

OTHER PUBLICATIONS

Commercon et al., "Tetrahedron Letters", vol. 33, No. 36, pp. 5185–5588, 1993.
Ojima, I. et al., J. Med. Chem. 1997, 40, 267–278.
Tetrahedron Letters, 34(13), 2047–2050, (1993), L.L. Klein.
Bio. Org. Med. Chem. Lett.12, pp. 1429–1432 (1994), C.J. Maring et al.
J. Org. Chem., 56, 6939–6942 (1991), J.N. Denis et al.
Pharmac. Ther. 52, 1–34 (1991), D.G.I. Kingston et al.
Anal. Rep. Med. Chem., 28, 305–314 (1993), M. Suffness.
Drugs of Future, 19(6), 573–584 (1994), M. Hepperle et al.
J. Chem. Soc., Perkin Trans I, pp. 2925–2929 (1992), G. Appendino et al.
Tetrahedron Letters, pp. 5173–5177 (1992), L.O. Zamir et al.
Chem & Eng. News., Apr. 12th, pp. 36–37 (1993).
J. Med. Chem.,37, 1408–1410 (1994), I. Ojima et al.

*Primary Examiner*—Ba K. Trinh
*Attorney, Agent, or Firm*—Ladas & Parry

[57] ABSTRACT

Novel taxane derivatives and intermediates having the formula 1.

and a process for the preparation of the compounds of the formula 1 from 14-β-hydroxy-10-deacetylbaccatin III of formula 2 and pharmaceutically acceptable compositions containing the taxane derivatives and intermediates of formula 1.

10 Claims, No Drawings

TAXANE DERIVATIVES FROM 14-β-HYDROXY-10 DEACETYLBACCATIN III

BACKGROUND OF THE INVENTION

1. Field of the Invention

The present invention relates to novel taxane derivatives and intermediates having the general formula 1.

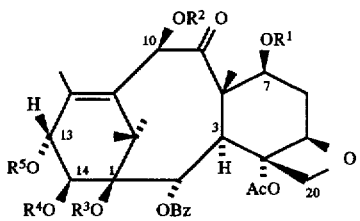

In the above formula 1, $R^5$ represents hydrogen, lower alkyl, unsubstituted or substituted phenyl, tri(alkyl or phenyl)silyl, lower alkanoyl, substituted alkanoyl or amino alkanoyl and can also represent a group having the formula 3,

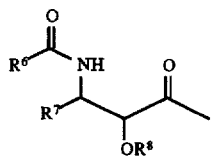

in which $R^6$ is hydrogen, lower alkyl, unsubstituted or substituted phenyl, lower alkoxy, substituted alkoxy, amino, or substituted amino; $R^7$ is hydrogen, lower alkyl, unsubstituted or substituted phenyl, hydroxy alkyl, alkoxy alkyl, or aminoalkyl and $R^8$ is hydrogen, lower alkyl, lower alkanoyl, substituted alkanoyl, or amino alkanoyl. In the compound of the formula 1, $R^1$, $R^2$, $R^3$ and $R^4$ represent independently hydrogen, lower alkyl, alkanoyl, substituted alkanoyl, or $OR^1$ and $OR^2$ taken together and/or $OR^3$ and $OR^4$ taken together can independently form a cyclic ring having the formula 4,

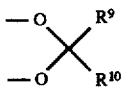

where $R^9$ and $R^{10}$ are independently hydrogen, lower alkyl, phenyl or substituted phenyl, lower alkoxy, amino, substituted amino or $R^9$ and $R^{10}$ can be taken together as a single atom such as oxygen or sulfur having respectively the formulas 4a and 4b,

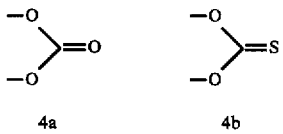

wherein at least one of $R^1$, $R^2$, $R^3$, $R^4$ and $R^5$ is a substituent other than hydrogen; wherein $R^3$ and $R^4$ taken together are not a cyclic ring of formula 4 where $R^9$ and $R^{10}$ are methyl and $R^1$, $R^2$ and $R^5$ are hydrogen; wherein when $R^1$ and $R^2$ are each $CCl_3CH_2CO_2$ and when $R^3$ and $R^4$ taken together are formula 4a, $R^5$ is not hydrogen; wherein when $R^3$ and $R^4$ taken together are formula 4a and $R^5$ is a group of formula 3, where $R^6$ is alkoxy, $R^7$ is phenyl, $R^8$ is not hydrogen; and wherein when $R^5$ is a group of Formula 3 where $R^8$ is H, $R^7$ is phenyl, and $R^6$ is phenyl or $OBu^t$, at least one of $R^1$, $R^2$, $R^3$ or $R^4$ is not hydrogen The compounds of the formula 1 are prepared from 14-β-hydroxy-10-deacetylbaccatin III having the formula 2, isolated from a plant from a plant of the 'taxus genus'.

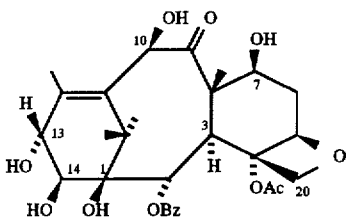

2. Description of the Related Art

Taxol, one of the terpenes isolated from the plant *Taxus brevifolia*, has gained worldwide attention in recent years because of its potential anti-tumor activity against a broad spectrum of tumor types. This compound has also obtained U.S. FDA approval for the treatment of ovarian cancer. However, due to serious limitations encountered in its supply primarily from the extraction of the bark of a slow growing pacific yew tree *Taxus brevifolia*, semi-synthetic efforts from an abundantly available natural precursor, 10-deacetylbaccatin III, have emerged and gained prime importance to improve the supply of taxol for further investigations. Also simultaneously, Structure Activity Relationship (SAR) studies on taxol have been undertaken by several groups and reviewed recently [D.G.I. Kingston, Pharmac. Ther. 52, 1 (1991); D.G.I. Kingston et. al., The Taxane Diterpenoids, in The Progress in the Chemistry of Organic Natural Products, Vol. 61, edited by W. Herz et.al., Springer-Verlag, N.Y. 1993; M. Suffness, Annl. Rep. Med. Chem. 1993, 28, 305– 314; G. I. George, Exp. Opin. Ther. Pat. 1994, 4, 109–120; G. I. George, Drugs Of Future, 1994, 19(6), 573–584;].

During the search for natural resources for the compounds having the core structure of taxol, two new compounds namely, 14β-hydroxy-10-deacetylbaccatin III of the formula 2 from the plant T. Wallichiana [J. Chem. Soc., Perkin Trans 1, 2925–2929 (1992)] and 9-dihydro-13-acetylbaccatin III of the formula Y,

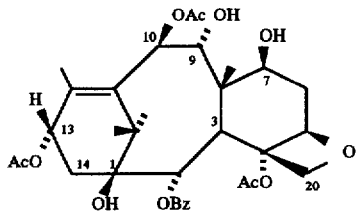

from the plant *T. Canadensis* [Tetrahedron Lett., 33, 5173 (1992)] have been isolated recently and used as precursors in the preparation of semi-synthetic analogues of taxol [EP 0 559 019A1; I. Ojima, J. Med. Chem., 1994, 37, 1408–1410; C & E News, 12th Apr., 36 (1993); PCT Intl. WO 93/21173; Tetrahedron Lett., 1993, 34, 2047–2050; Bio. Org. Med. Chem. Lett., 1994, 4, 1429–1432]. According to these reports and patent applications, some of the synthetic analogues of taxol prepared from 14-β-hydroxy-10-deacetylbaccatin III of the formula 2 and 9-dihydro-13-acetylbaccatin III of the formula Y have exhibited water solubility and superior anti-tumor activity than taxol against certain cell lines. One of the taxol derivatives having the formula Z,

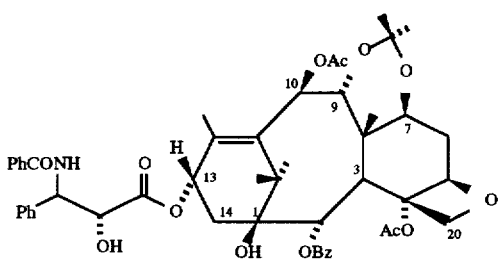

wherein 7, 9-hydroxyls were tied up as acetonide, was prepared from 9-dihydro-13-acetylbaccatin III, having the formula Y, and has exhibited anti-tumor activity comparable to taxol against P388 and A549 cell lines as reported in PCT Intl. WO 93/21173. Also based on the pharmacological data available on various taxol analogues made so far, it was revealed that the polar and bulky substituents on the C-7 hydroxyl group and acylation or deacylation at C-10 hydroxyl lack major impact on taxol activity.

DETAILED DESCRIPTION OF THE INVENTION

Considering all these factors, we focused our studies to prepare novel taxane derivatives of formula 1, as defined above, from 14-β-hydroxy-10-deacetylbaccatin III having the formula 2, presuming that these analogues may possess better water solubility and bioavailability which in turn may modify undesirable toxicity. The compounds of the formula 1, as defined above, involving 7,10-hydroxyls tied up as acetonide with an additional free hydroxyl group at C-14 carbon possess superior pharmacological properties and can impart better biological activity profile. Also, the free hydroxyls at C-1 and C-14 carbons in the compounds of general formula 1 would be advantageous for further derivatization leading to novel analogues with improved water solubility and reduced toxicity.

The present invention particularly includes the compounds of the formula 1 wherein $R^1$, $R^2$, $R^3$ and $R^4$ have the meaning described above and $R^5$ represents the side chain of taxol, having the formula 3,

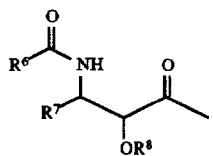

wherein $R^6$, $R^7$ are phenyl and $R^8$ is hydrogen and also the side chain of taxotere having the formula 3 wherein $R^6$ is tert-butoxy, $R^7$ is phenyl and $R^8$ is hydrogen.

The terms representing $R^1$ through $R^{10}$ in these compounds have the following definitions throughout the present invention.

The term 'lower alkyl' denotes a univalent, branched or straight hydrocarbon chain containing 1 to 8 carbon atoms. Representative of the alkyl groups are methyl, ethyl, propyl, isopropyl, butyl, sec.butyl, tert.butyl, pentyl, iso pentyl, tert. pentyl, hexyl, isohexyl and octyl.

The term 'lower alkoxy' denotes lower alkyl groups which are connected to the rest of the molecule through oxygen linkage. Representative of the alkoxy groups are methoxy, ethoxy, propoxy, isopropoxy, and tert.butoxy.

The term 'haloalkoxy' denotes halogens, preferably fluorine or chlorine attached to alkoxy groups. Representative of the haloalkoxy groups are trichloroethoxy, trichloromethoxy, difluoromethoxy, and trifluoromethoxy.

The term 'alkanoyl' denotes an alkyl group as defined above attached via a carbonyl group to the rest of the molecule. Representative of the alkanoyl groups are acetyl, propionyl, butanoyl, pentanoyl and isopentanoyl.

The term 'aminoalkanoyl' represents the alkyl groups, as defined above, substituted with amino groups such as 2-aminopropanoyl or 4-aminobutanoyl. The amino groups may also be mono or disubstituted.

The term 'substituted' alkoxy, alkanoyl, alkyl, amino or phenyl group used in the present invention refers to those substituents which can be selected from groups such as hydroxyl, alkyl, alkoxy, thioalkoxy, benzyloxy, carboxyl, amino, alkylamino and halogen. It is preferred that the halogen is chlorine, iodine, bromine or fluorine.

According to the present invention there is provided a process for the preparation of the novel taxane derivatives and intermediates of the general formula 1,

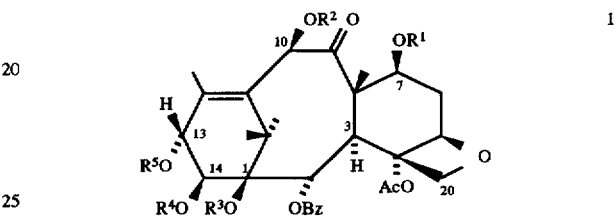

wherein $R^5$ represents hydrogen, lower alkyl, unsubstituted or substituted phenyl, tri(alkyl or phenyl)silyl, lower alkanoyl, substituted alkanoyl or amino alkanoyl and can also represent a group having the formula 3,

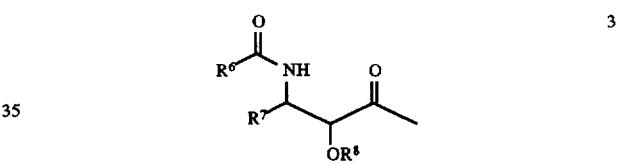

in which $R^6$ is hydrogen, lower alkyl, unsubstituted or substituted phenyl, lower alkoxy, substituted alkoxy, phenoxy, substituted phenoxy, amino, or substituted amino; $R^7$ is hydrogen, lower alkyl, unsubstituted or substituted phenyl, hydroxy alkyl, alkoxy alkyl, or aminoalkyl and $R^8$ is hydrogen, lower alkyl, lower alkanoyl, substituted alkanoyl, or amino alkanoyl; $R^1$, $R^2$, $R^3$ and $R^4$ represent independently hydrogen, lower alkyl, lower alkanoyl, or substituted alkanoyl or $OR^1$ and $OR^2$, taken together and/or $OR^5$ and $OR^4$ taken together can independently form a cyclic ring having the formula 4,

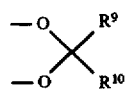

where $R^9$ and $R^{10}$ are independently hydrogen, lower alkyl, phenyl, substituted phenyl, lower alkoxy, amino, substituted amino or $R^9$ and $R^{10}$ may be taken together as a single atom such as oxygen or sulfur having respectively the formula 4a or 4b,

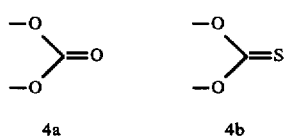

from 14-β-hydroxy-10-deacetylbaccatin III having the formula 2, which comprises, (i) reacting 14-β-hydroxy-10-deacetylbaccatin III of the formula 2 with a compound of the formula 5 or 6

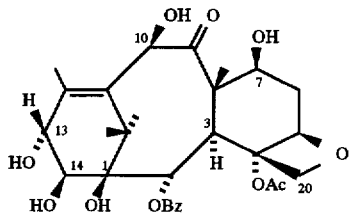

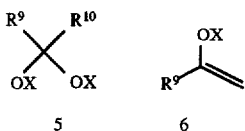

wherein $R^9$ and $R^{10}$ have the meaning given above and X represents an alkyl group having 1–3 carbon atoms or the two X together can form a cyclic ring, to give a compound of the formula 7,

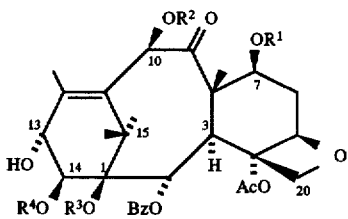

in which $R^1$ & $R^2$ and $R^3$ & $R^4$ together, or $R^1$ & $R^2$ together or $R^3$ & $R^4$ together can form a cyclic ring leaving a free hydroxyl group at the C-13 position;

(ii) reacting the compound of the formula 7 as prepared in step (i) with a compound of the formula 8,

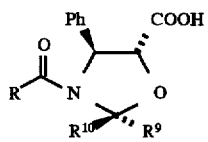

where R represents lower alkyl, lower alkoxy, substituted or unsubstituted phenyl, amino, substituted amino or heterocyclic rings such as pyridine, furan, or thiophene, and $R^9$ and $R^{10}$ have the meaning described above, to obtain a compound of the formula 9;

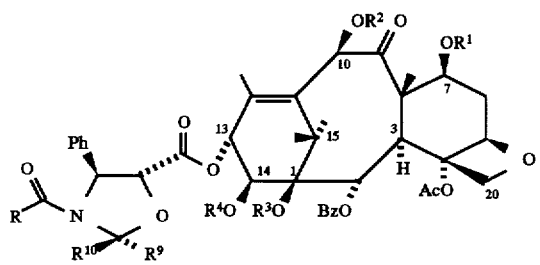

(iii) hydrolysing the cyclic groups present in the compounds of the formula 9 by conventional methods to obtain the compounds of the formula 10,

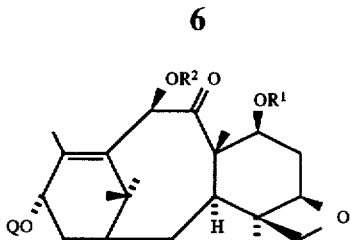

wherein Q represents the group of the formula U or V,

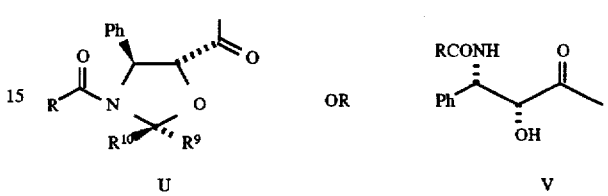

wherein R, $R^1$, $R^2$, $R^9$ and $R^{10}$ have the meaning given above; and (iv) converting the compounds of the formula 10, as prepared in the step (iii), by conventional methods to compounds of the general formula 1 as defined above.

In general, the compounds of the formula 1 may be synthesized starting from compound of the formula 2 by a series of steps as illustrated in the Schemes A–H referred to hereinafter. The preparation of the compounds of the formula 7 wherein $R^1$ & $R^2$ together, or $R^3$ & $R^4$ together or both $R^1$ & $R^2$ together and $R^3$ & $R^4$ together can form a cyclic ring, from the 14-β-hydroxy-10-deacetylbaccatin III of the formula 2 as mentioned in step (i) of the process of the present invention is a novel transformation in which the four hydroxyl groups at the carbons C-1, C-14, C-7 and C-10 of the compound of the formula 2 are tied up as cyclic rings in one step leaving the hydroxyl group free at the position C-13 for further derivatization with a variety of reagents. For instance, diacetonides of the formula 7, where $R^1$ & $R^2$ and $R^3$ & $R^4$ can form cyclic ring systems, as described in the step (i), can be prepared by reacting 14-β-hydroxy-10-deacetylbaccatin III of the formula 2, in the presence of an acid, with dialkyl acetal of an appropriate aldehyde or ketone of the formula 5,

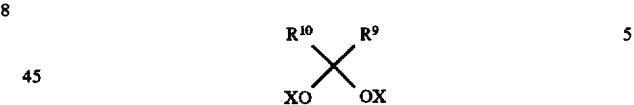

wherein $R^9$, $R^{10}$ and X have the meanings given above and recovering the compound of the formula 7 by known methods. The ketone or aldehyde of the dialkylacetal employed in the reaction may be selected from acetone, propanone, butanone, methyl ethyl ketone, ethyl vinyl ketone, methyl benzyl ketone, acetophenone, benzaldehyde, acetaldehyde and propionaldehyde.

Alternatively, compound of the formula 2 may also be reacted, in the presence of an acid, with enol-ethers of appropriate methyl ketones having the formula 6,

where $R^9$ and X have the meanings given above and recovering the appropriate compound of the formula 7 by known methods. The methyl ketones of the corresponding enol-ethers employed in the reaction may be selected from acetone, 2-butanone, methyl propyl ketone, pentan-2-one, methyl vinyl ketone, methyl benzyl ketone, and acetophenone.

The above said reactions may preferably be affected at a temperature in the range of 0° to 100° C. The reaction mixture may contain oraganic solvents such as benzene, toluene, xylene, chloroform, dichloromethane, dichloroethane, acetonitrile and 1,4-dioxane. The acids such as p-toluenesulfonic acid, pyridinium-p-toluenesulfonic acid, camphorsulphonic acid, trifluoroacetic acid, formic acid and perchloric acid may be employed in this reaction.

To illustrate the above said reaction, compound of the formula 2 is reacted with an excess of 2,2-dimethoxypropane in the presence of pyridinium p-toluenesulfonate (PPTS) to provide the diacetonide derivative having the formula 11 in which four hydroxyl groups at C-1, C-14, C-7 and C-10 carbon atoms were tied up as acetonide rings as shown in the Scheme A. The free hydroxyl group at C-13 position in the compounds of the formula 7 may be utilized to make simple esters or ethers which may also be expected to possess anti-cancer activity. For example, compound such as 13-acetoxy diacetonide of the formula 12 can be prepared by the reaction of compound of the formula 11 with acetic anhydride in pyridine, Scheme A.

SCHEME B

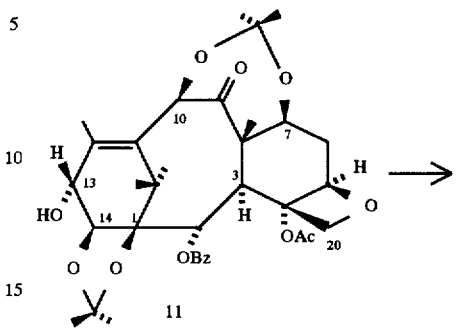

SCHEME A

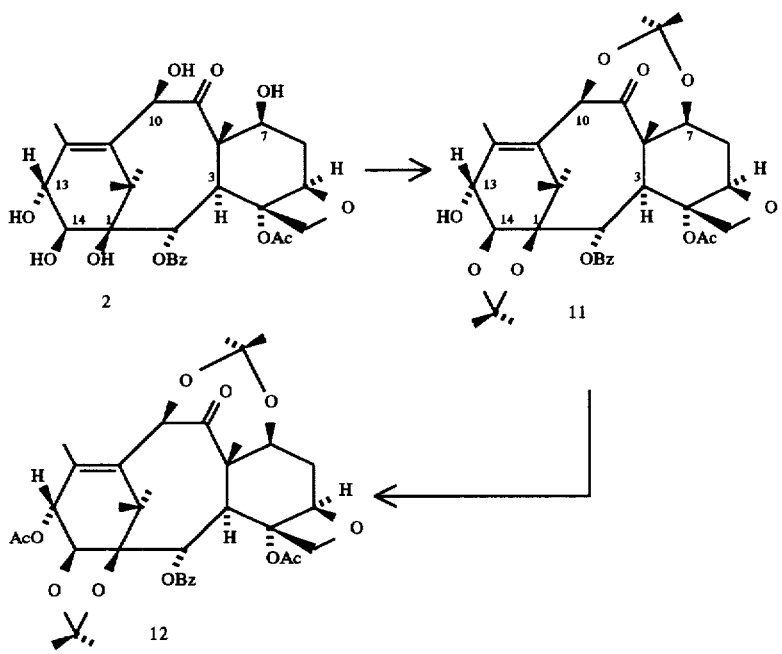

To prepare compounds of the formula 7 having dissimilar acetonides at C1, C14 and C7, C10 or acetonide at C7, C10 and carbonates or independent esters at C1 or C14, compound of the formula 7 is partially hydrolysed by means of mild acid at a temperature in the range of 0° to 400° C. The acid used for this purpose can be inorganic or organic acid such as hydrochloric acid, sulfuric acid, acetic acid, -trifluoroacetic acid, formic acid dissolved in water or organic ethereal solvent such as diethyl ether, tetrahydrofuran, or 1,4-dioxane. For example, hydrolysis of diacetonide of the formula 11 under mild acid conditions produced 7,10-acetonide of the formula 13. Similarly, compound of the formula 12 can also be partially hydrolysed using 2% HCl to obtain 13-acetoxy-7,10-acetonide 14, Scheme B.

-continued
SCHEME B

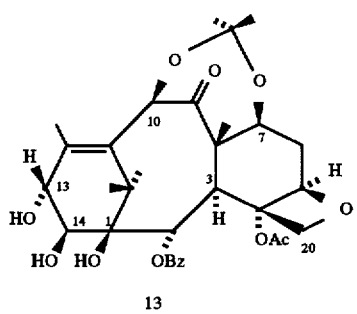

-continued
SCHEME B

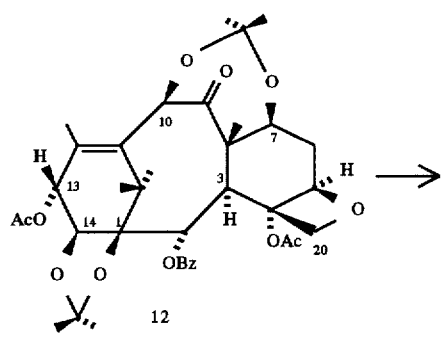

12

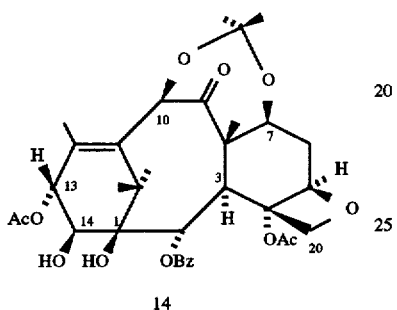

14

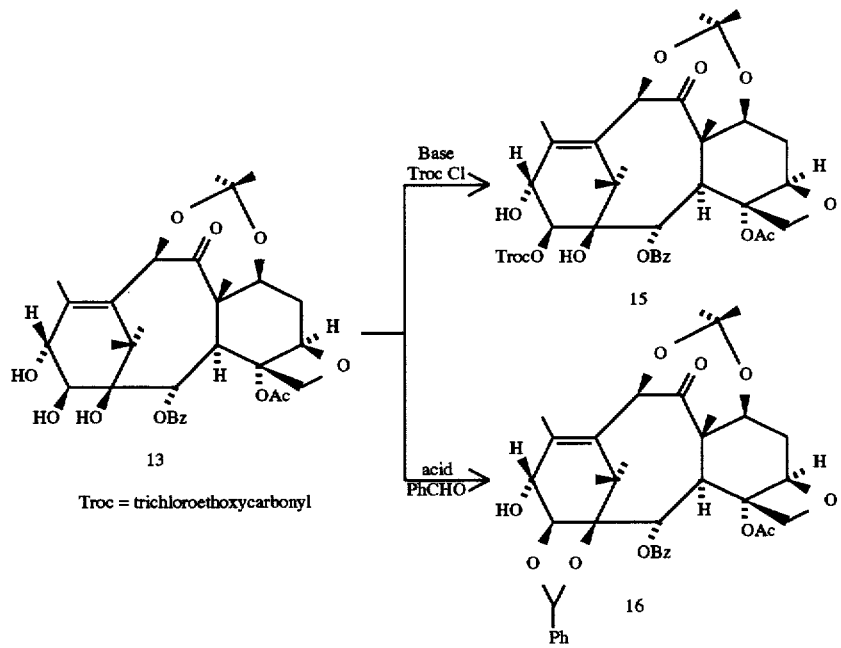

Troc = trichloroethoxycarbonyl

The free hydroxyl groups at C-1 and C-14 carbons in the compounds of the formula 7 can be protected together as carbonate or thiocarbonate or individually as in the formula 15, Scheme C, using reagents such as phosgene, diethylcarbonate, carbonyl diimidazole, thiocarbonyl diimidazole, or trichloroethyl chloroformate, in the presence of a base such as pyridine, triethylamine, diisopropylamine, or dimethylaminopyridine and solvents such as benzene, toluene, or tetrahydrofuran or chlorinated solvents such as dichloromethane or chloroform. For example, reaction of 7,10-acetonide of the formula 13 with trichloroethyl chloroformate in pyridine produced Troc (trichloroethoxycarbonyl)-protected compound 15 as shown in the Scheme C.

Similarly, the free hydroxyl groups at C-4, C-14 in the compounds of the formula 13 can also be tied up in cyclic form which is different from that of C7, C10-acetonide to generate compounds having dissimilar cyclic rings such as formula 16 using the method described above. Scheme C.

The free hydroxyl group present in all these compounds of the formulae 11–16 can be best utilized now to add suitable side chains having the formula 3 in step (ii) of the process described above.

In step (ii) of the process of the present invention, the compounds of the formula 7 are reacted with the compounds of the formula 3. In order to attach the group of the formula 3 at C-13 carbon of the formula 7, it is necessary to use the protected form of the formula 3 such as an oxazolidine derivative having the formula 8, where R, $R^9$ and $R^{10}$ have the meaning described above.

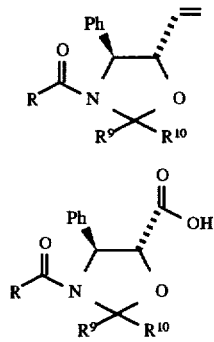

The oxazolidine acid of the general formula 8 may be obtained from the corresponding alkene derivative of the formula 17 by using standard oxidation conditions, preferably using $RuCl_3$—$NaIO_4$ in acetonitrile-water- carbontetrachloride solvent mixture at a temperature in the range of 10°–40° C.

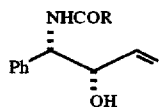

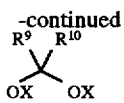

The compound of the formula 17 may be prepared via oxaxolidine ring formation of compound of the formula 18 on treatment with reagents of the formula 18 in which $R^9$, $R^{10}$ and X have the meanings mentioned above. In general, this reaction can be carried out using dialkylacetal of an aldehyde or ketone in an organic solvent such as benzene, chloroform, toluene, or dichloromethane in the presence of an acid such as p-toluenesulfonic acid, pyridinium p-toluenesulfonic acid, camphorsulfonic acid, trifluoroaceric acid, acetic acid, or perchloric acid at a temperature between 20°–100° C. The ketone or aldehyde of the dialkylacetal employed in the reaction may be selected from acetone, propanone, butanone, methyl ethyl ketone, methyl vinyl ketone, methyl benzyl ketone, acetophenone, benzaldehyde, substituted benzaldehyde, acetaldehyde, or propionaldehyde. The compound of the formula 18 is prepared according to the method described in J. Org. Chem., 56, 6939(1991) by Andrew Green et al.,.

For example, diacetonide of the formula 11 was treated with an oxazolidine acid of the formula 8a in the presence of a base to deliver the ester of the formula 19. Similarly, reaction of diacetonide of the formula 11 with an oxazolidine acid of the formula 8b produced a compound of the formula 20, Scheme D.

SCHEME D

The solvent used in the reaction may be selected from hexane, benzene, toluene, xylenes, chloroform, acetonitrile, N,N-dimethylformamide, dichloroethane, or dichlorobenzene. The base used in the reaction may be chosen from pyridine, triethylamine, diethylcyclohexylamine, diisopropylethylamine, dicyclohexylcarbodiimide, dipyridylcarbonate, or 4-dimethylaminopyridine. The reaction may preferably affected at a temperature in the range of 40°–150° C.

In step (iii) of the process of the present invention, the compounds prepared in step (ii) were hydrolysed by conventional methods to deliver the compounds of the formula 10 having free hydroxyl groups at C-1 and C-14 carbons. For example, partial hydrolysis of the compound of the formula 19, using a mild acid, gave compound of the formula 21. Similarly, compound of the formula 20 upon partial hydrolysis provided compound of the formula 22, Scheme E.

However, complete hydrolysis of compound of the formula 19 furnished the requisite ester of the formula 23 having a taxol side chain at C-13 carbon, Scheme E.

Similarly, compound of the formula 20, upon complete hydrolysis produced the requisite ester of the formula 25 having a taxotere side chain via an amino alcohol 24. The acids used for this purpose can be selected from inorganic or organic acids such as hydrochloric acid, sulfuric acid, acetic acid, p-toluenesulfonic acid, formic acid, trifluoroacetic acid, methanesulforic acid, or camphorsulfonic acid dissolved in water or organic solvents such as benzene, toluene, diethyl ether, tetrahydrofuran, or 1,4-dioxane or chlorinated solvents such as chloroform, or dichloromethane. The bases used in the conversion of amino alcohol of the formula 24 to an amide of the formula 25 may be selected from the inorganic bases such as sodium bicarbonate, sodium carbonate, potassium carbonate, cesium carbonate, or lithium carbonate or organic bases such as pyridine, triethylamine, 4-dimethylaminopyridine, or diisopropylamine. The solvent used for this purpose may be selected from benzene, toluene, diethyl ether, tetrahydrofuran, dimethoxyethane, chloroform, dichloromethane, ethyl acetate, or acetonitrile. BOC is tert.butoxy carbonyl.

SCHEME E

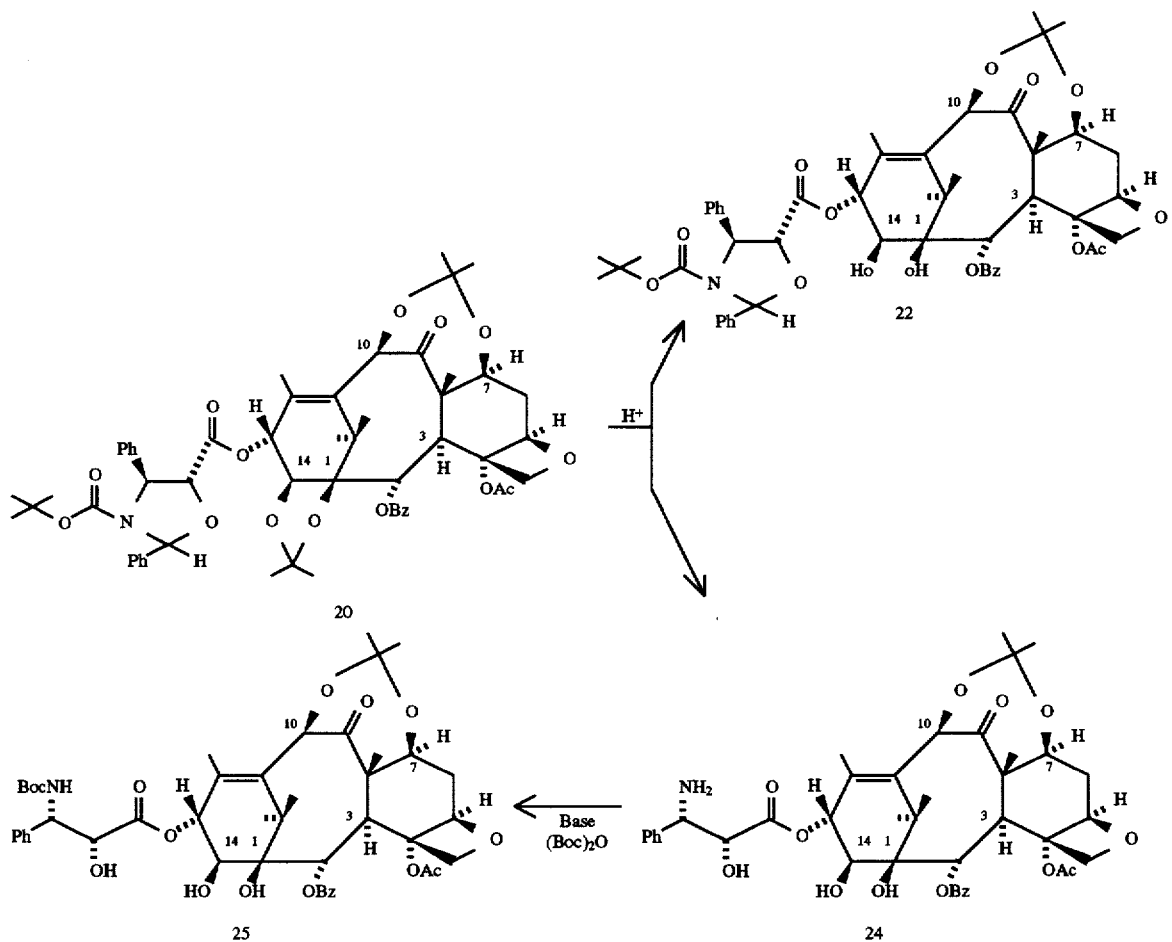

-continued
SCHEME E

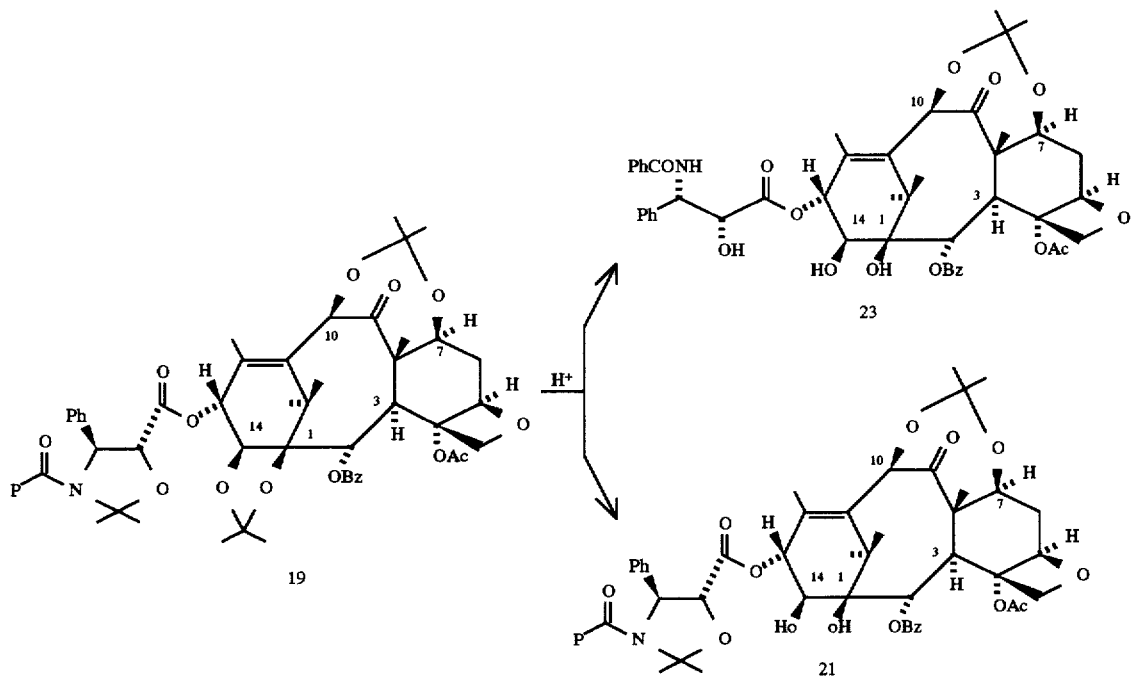

In step (iv) of the process of the present invention, the free hydroxyl groups at C1, C14 in the compounds of the formula 10 obtained in step (iii) is refunctionalized to prepare compounds of the general formula 1.

For example, compound of the formula 21 was treated with trichloroethylchloroformate(Troc-Cl) in the presence of a base such as pyridine to obtain ditroc derivative of the formula 26 which upon acid hydrolysis produced the compound of the formula 27 having taxol side chain at C-13 and free hydroxyls at C-7 & C-10 positions as shown in the Scheme F. Similar set of reactions were carried out on the compound of the formula 21b to obtain compound of the formula 30, via the compound of the formula 29, Scheme F, having taxotere side chain at C-13 and free hydroxyl groups at C-7 and C-10 positions. The acids used in the hydrolysis reaction can be selected from inorganic or organic acids such as hydrochloric acid, sulfuric acid, acetic acid, p-toluenesulfonic acid, formic acid, trifluoroacetic acid, methanesulfonic acid, or camphorsulfonic acid. Removal of Troc-group in the compounds of the formulae 27 and 30 using zinc-acetic acid provided 14-β-hydroxy-10-deacetyl taxol of the formula 28 and 14-β-hydroxy taxotere of the formula 31 respectively, Scheme F.

SCHEME F

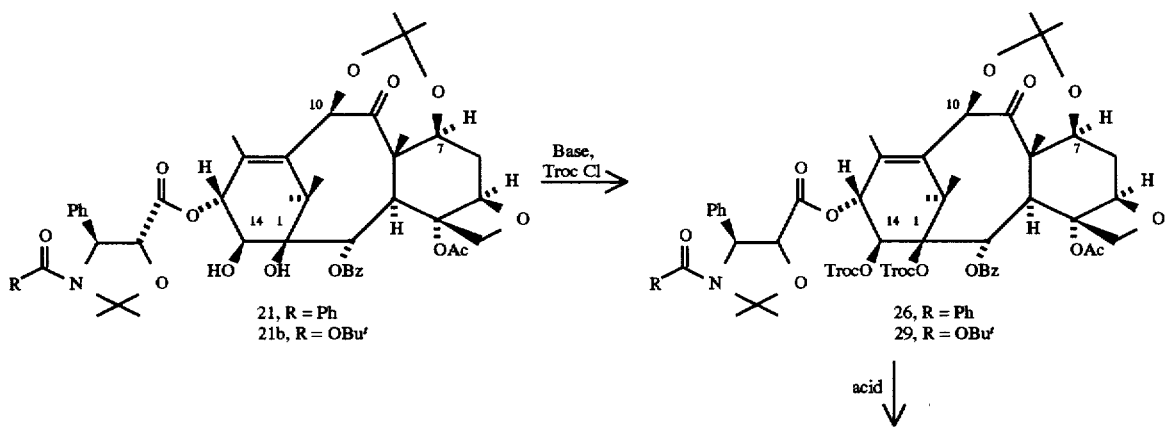

-continued
SCHEME F

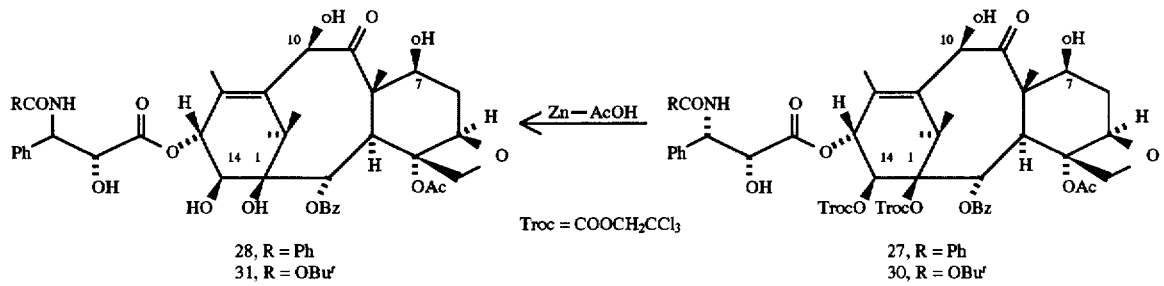

28, R = Ph
31, R = OBu'

Troc = COOCH₂CCl₃

27, R = Ph
30, R = OBu'

Also compounds of the formula 32 having dissimilar acetonides at C7, C10 and C1, C14 carbons, can be obtained by the reaction of the compound of the formula 23 with a reagent having the formula 5($R^9$=Ph,$R^{10}$=H,X=Me) using the similar conditions described in step(i) of the process, Scheme G.

SCHEME G

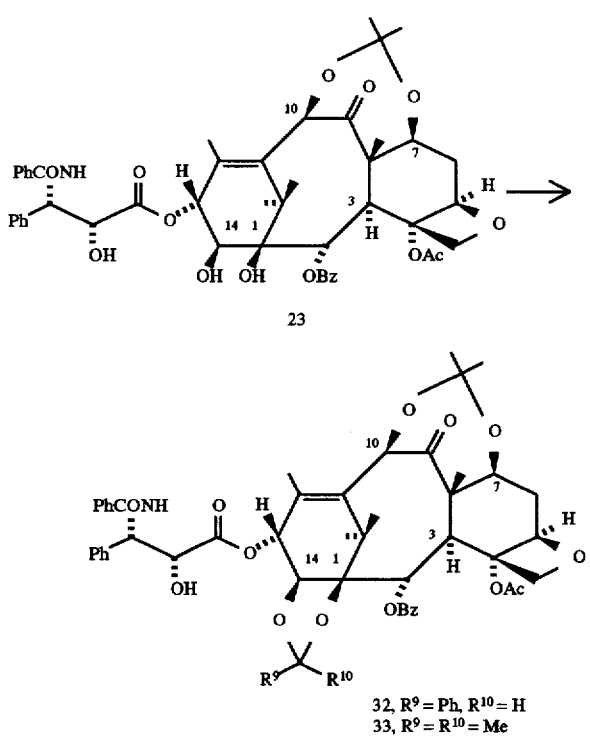

32, $R^9$ = Ph, $R^{10}$ = H
33, $R^9$ = $R^{10}$ = Me

Now, to prepare the compounds having C-14 ester side chains leaving the free hydroxyl group at C-13 position in the compounds of the formula 1, an oxazolidine acid of the formula 8 was treated with compounds of the formula 7, wherein $R^1$ & $R^2$ together can form a cyclic ring, using the similar reaction conditions described in the step (ii) of the process. For example, compound of the formula 13 dissolved in an organic solvent when treated with an oxazolidine acid 8a in the presence of a base delivered exclusively the compound of the formula 34, having an ester at C-14 position. Similarly, reaction of the compound of the formula 13 with an oxazolidine acid 8c produced the C-14 ester 36, Scheme H.

Once again the solvent used in the reaction may be selected from hexane, benzene, toluene, xylene, chloroform, acetonitrile, N,N-dimethylformamide, dichloroethane, or dichlorobenzene and the base used in the reaction may be chosen from pyridine, triethylamine, diethylcyclohexylamine, diisopropylethylamine, dicyclohexylcarbodiimide, dipyridylcarbonate, or 4-dimethylaminopyridine. The reaction may preferably be effected at a temperature in the range of 40°–150 °C. Acid hydrolysis of oxazolidine ring in the compounds of the formula 34 gave the compound of the formula 35 having a taxol side chain at C-14 and a free hydroxyl group at C-13 positions. Similarly, reaction of the compound of the formula 36 with a mild acid furnished the ester of the formula 37 having a taxotere side chain at C-14 and a free hydroxyl group at C-13 positions, Scheme H.

SCHEME H

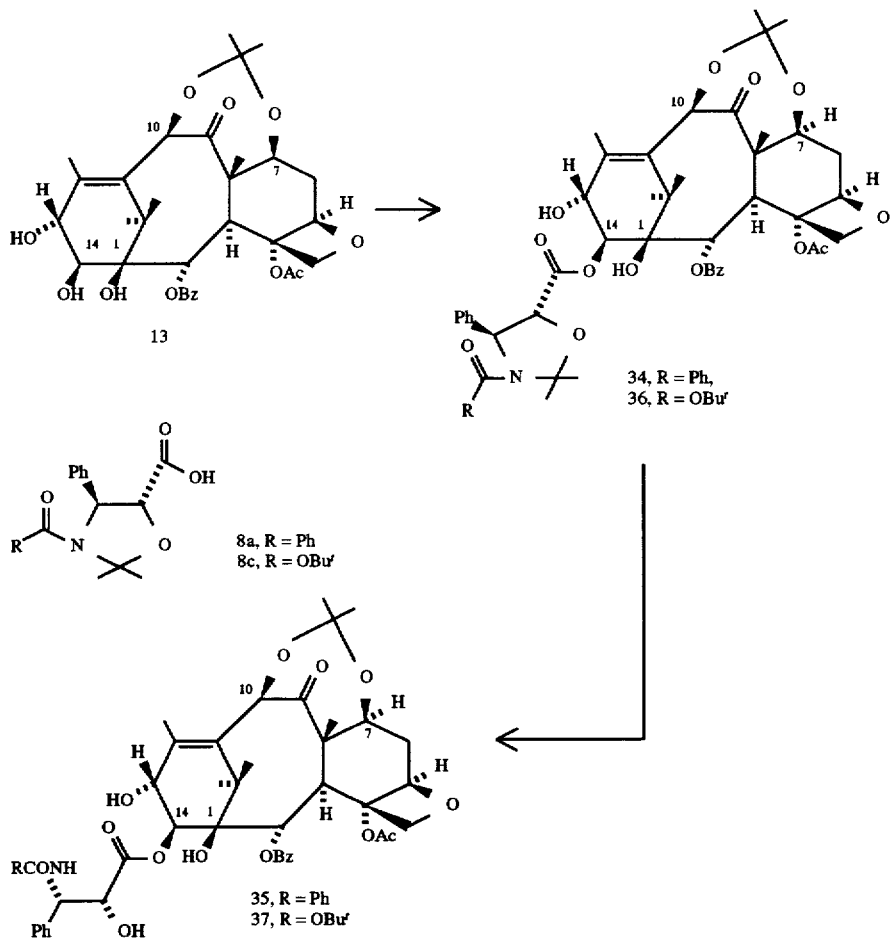

The acids used for this purpose can be selected from inorganic or organic acids such as hydrochloric acid, sulfuric acid, acetic acid, formic acid, p-toluenesulfonic acid, trifluoroacetic acid, methanesulfonic acid, or camphorsulfonic acid dissolved in water or organic solvents such as diethyl ether, tetrahydrofuran, or 1,4-dioxane or chlorinated solvents such as chloroform, or dichloromethane.

In conclusion, the present invention provides a number of novel compounds related to taxane family. In particular, these compounds are related to taxol, the recently FDA approved anticancer drug, and its various analogues having an additional hydroxyl group at C-14 position of the taxane skeleton. In fact, preferred compounds 21 and 23 showed good selectivity and sensitivity towards leukemia, colon cancer and ovarian cancer cell lines. Selectivity and sensitivity were particularly good at 0.01 to 1 µm concentrations at GI50 level (concentrations of the agent in the assay that produced 50 0 growth inhibition). In particular, compound 23 displayed excellent selectivity and sensitivity towards three leukemia cell lines ($IC_{50}$<0.1 µm), four colon cancer cell lines ($IC_{50}$≦0.2 µm), three ovarian cancer cell lines ($IC_{50}$<1 µm) and five other breast cancer cell lines at GI50 (≦0.1 µm) and TGI (0.1 to 10 µm) levels. (TGI is total growth inhibition). These results are shown in Example 23. These results were obtained by carrying out experiments according to National Cancer Institute protocols.

Other preferred compounds such as 25, 27, 30, 32, 33, 35 and 37 prepared in the present invention are also expected to posses improved anticancer and anti-viral activity. Compounds 28 and 31 are also preferred.

All these compounds of the general formula 1 of the present invention, including the pharmaceutically acceptable salts thereof and the compositions containing them, are useful as anti-cancer and anti-viral agents. Administration of the active compounds of the formula 1, in pure form or in an appropriate pharmaceutical composition can be carried out via any of the accepted modes of administration for serving similar utilities. Thus, administration can be, for example, orally, nasally, parenterally or topically, in the form of solid, semi-solid, lyophilised powder, or liquid dosage forms, such as for example, tablets, suppositories, pills, capsules, powders, solutions, suspensions, emulsions, creams, lotions, aerosols, ointments or the like, preferably, in unit dosage forms suitable, for simple administration of precise dosages. The compositions may include a conventional pharmaceutical carrier, diluent or excipient and an active compound of general formula 1 and, in addition, the compositions may include either medicinal agents, pharmaceutical agents, carriers, adjuvants, etc.

The invention is described in detail with specific examples given below to enable those skilled in the art to more clearly understand and practice the invention. They are provided by way of illustration and representation only and should not be considered to limit the scope of the invention.

EXAMPLE 1

Preparation of Dimethyl diacetonide of the formula 11

A solution of 80 mg of 14 hydroxy-10-deacetylbaccatin III of the formula 2 in 5 ml of 2,2-dimethoxypropane was heated to reflux in the presence of 6 mg of pyridinium p-toluenesulfonate with continuous stirring. The reaction was quenched with pyridine and diluted with chloroform. The organic layer was washed with 5% sodium bicarbonate solution, brine and dried over anhydrous sodium sulfate. Concentration of the solvent and purification of the residue over a silica gel (60–120 mesh) chromatographic column using ethyl acetate- chloroform solvent mixture as eluent afforded 40 mg of diacetonide of the formula 11. mp: 222°–223° C.; IR: 3483, 1719, 1272, 1058, 710 cm$^{-1}$; $[\alpha]_D$ at 34° C. =+31.5 (c 0.20,CHCl$_3$); $^1$H NMR (CDCl$_3$, 200 MHz): δ 8.14 (d, J=7.4 Hz, 2H), 7.68–7.39(m,3H), 6.21(d, J=5.6 Hz,1H), 5.31(s,1H), 4.96 (br s, 1H), 4.78(br s, 1H), 4.71(t, J=7.6 Hz, 1H), 4.37(d, J=7.8 Hz, 1H), 4.10(dd, J=5.4 Hz,2H), 4.01(d, J=7.4 Hz, 1H), 2.65(d, J=7.4 Hz, 1H), 2.23(m,1H), 2.36(s,3H), 2.12(s,3H), 1.79(m,1H), 1.69(s, 3H), 1.61(s,3H), 1.53(s,3H), 1.38(s,3H), 1.31(s,3H), 1.09(s, 3H), 1.01(s, 3H); $^{13}$C NMR (CDCl$_3$): δ 214.19, 171.18, 165.70, 138.08, 133.29, 132.24, 130.40, 130.00 (2C), 128.48 (2C), 112.97, 109.39, 88.26, 836.40, 83.66, 83.25, 78.92, 78.71, 76.17, 74.75, 70.75, 53.56, 41.60, 36.64, 31.18, 27.52, 27.19, 26.79, 25.77, 24.79, 23.27, 22.54, 16.83 and 14.29; FABMS: 641.2988 [M+H]$^+$.

EXAMPLE 2

Preparation of 7,10-monoacetonide of the formula 13

50 of dimethyl diacetonide of the formula 11, as prepared in the example 1, was dissolved in 5 ml of tetrahydrofuran and treated with 5 ml of 10% HCl with continuous stirring at 25° C. until the starting material was disappeared. Reaction mixture was quenched with sodium bicarbonate solution and extracted with ethyl acetate. The resulting organic layer was dried and concentrated to get 45 mg of solid residue as 7,10-monoacetonide of the formula 13. mp: 217°–218° C.; IR: 3548, 3450, 1714, 1260, 1060, 715cm$^{-1}$; $[\alpha]_D$ at 25° C. −34.0 (c 0.2, CHCl$_3$); $^1$H NMR (CDCl$_3$,200 MHz): δ 8.14(d, J=7.2 Hz, 2H), 7.65–7.41 (m, 3H), 6.13 (d, J=6.8 Hz, 1H), 5.51 (s,1H), 4.97(m, 1H), 4.82(br s, 1H), 4.67(d,J=12 Hz,1H), 4.55(d, J=8.8 Hz,1H), 4.35(dd, J=4.9 Hz, 2H), 4.08(d,J=6.6 Hz, 2H), 3.61 (br s, 1H), 2.53 (br s, 1H), 2.41 (s,3H), 2.40–2.25 (m, 1H), 2.01(s,3H), 1.95–1.80 (m, 1H), 1.61 (s,3H), 1.37(s, 3H), 1.14 (s,3H), 1.11(s,3H), 0.99 (s,3H); $^{13}$C NMR (CDCl$_3$): δ 214.94, 172.46, 165.51, 139.01, 135.37, 133.57, 130.40(2C), 129.91, 128.60(2C), 109.66, 88.80, 83.42, 82.78, 82.06, 78.17, 75.50, 74.37, 70.12, 57.69, 41.96, 41.31, 35.55, 28.42, 28.08, 27.02, 22.65, 21.10, 16.32, 15.48; FABMS: 601.2621 [M+H]$^+$.

EXAMPLE 3

Preparation of 13-acetoxy-1,14,7,10-dimethyl diacetonido baccatin III of the formula 12

A mixture of 10 mg of dimethyl diacetonide of the formula 11, 1 ml of dry pyridine and 0.5 ml of acetic anhydride was dissolved in 5 ml of chloroform and stirred in the presence of 2 mg of 4,4-dimethylaminopyridine at 25° C. for 5 h. After the usual work up and concentration of the solvent produced 8 mg of the 13-acetoxy-1,14,7,10-dimethyl diacetonido baccatin III of the formula 12. mp: 95°–97° C.; $[\alpha]_D$ at 34° C. +20.00 (c 0.09, CHCl$_3$); IR: 1730, 1724, 1373, 1270, 1062, 894 cm$^{-1}$ ; $^1$H NMR (CDCl$_3$, 200 MHz): δ 8.20(d, J=7.4 Hz,2H), 7.71–7.42(m,3H), 6.28 (d, J=6 Hz, 1H), 6.18(d, J=3.2 Hz,1H), 5.32(s, 1H), 5.05(br s, 1H), 4.77(t, J=7.4 Hz, 1H), 4.39(d, J=7.6 Hz, 1H), 4.33(d, J=5 Hz, 1H), 4.02(d, J=7 Hz, 2H), 2.41(s, 3H), 2.36(m 1H), 2.31(s, 3H), 2.12(m, 1H), 1.94(s, 3H), 1.74(s, 3H), 1.66(s, 3H), 1.57(s, 3H), 1.44(s, 3H), 1.38(s, 3H), 1.31(s, 3H), 1.04(s, 3H); Mass (m/z): 683 (M+H).

EXAMPLE 4

Preparation of 13-acetoxy-7,10-acetonido baccatin III of the formula 14

10 mg of the 13-acetoxy-1,14,7,10-dimethyl diacetonido baccatin III of the formula 12, as prepared in the example 3, was dissolved in 2 ml of tetrahydrofuran and treated with 2 ml of 10% HCl at 25° C. for 2 h. Then the reaction was quenched with sodium bicarbonate and extracted with ethyl acetate. Concentration of the solvent afforded 8 mg of the 13-acetoxy-7,10-acetonido baccatin III of the formula 14 as a solid. mp: 114°–116° C.; $[\alpha]_D$ at 27° C.−49.00(c 0.1, CHCl$_3$); IR: 3456, 1725, 1253, 1060, 715 cm$^{-1}$; $^1$H NMR (CDCl$_3$, 200 MHz): δ 8.13 (d,J=7.2 Hz, 2H), 7.65–7.43 (m, 3H), 6.21(br s, 1H), 6.15(d, J=7 Hz, 1H), 5.46(s, 1H), 4.95(m, 1H), 4.54 (d, J=8.4 Hz, 1H), 4.48 (d, J=12 Hz, 1H), 4.35(m, 2H), 4.02 (d, J=6.8 Hz, 2H), 3.62 (br s, 1H), 2.48 (s, 3H), 2.42–2.22 (m,2H), 2.25(s,3H), 1.83(s,3H)I, 1.68(s,3H), 1.38(s, 3H), 1.22 (s, 3H), 1.16 (s,3H), 0.96 (s,3H); $^{13}$C NMR (CDCl$_3$): δ 214.50, 171.78; 169.78, 165.39, 136.54, 135.69, 133.60, 130.41(2C), 129.94 128.63(2C), 110.58, 96.09, 89.09, 82.82, 82.47, 80.31, 78.02, 75.47, 70.09, 57.75, 42.32, 41.13, 35.63, 28.53, 27.63, 27.22, 22.71, 21.27, 16.16, 14.92; Mass 643 (M+H).

EXAMPLE 5

Preparation of 14-troc-7,10-acetonido baccatin III of the formula 15

A mixture of 20 mg of 7,10-monoacetonide of the formula 13, 0.5 ml of pyridine and 0.1 ml of trichloroethyl chloroformate was heated to 80° C. until the starting material was consumed. The reaction mixture was cooled to room temperature and poured into ice water. The aqueous layer was extracted with ethyl acetate and washed with 5% HCl, water, brine and dried. Removal of solvent and purification of the resulting residue over silica gel column using hexane-ethyl acetate solvent as eluent provided 10 mg of 14-troc-7,10-acetonido baccatin III of the formula 15. IR: 3457, 1761, 1721, 1252, 1065, 840 cm$^{-1}$; $^1$H NMR(CDCl$_3$, 200 MHz): δ 8.15 (d,J=Hz, 2H), 7.65–7.42(m, 3H), 6.21 (s, 1H), 6.18 (d, 1H), 4.95 (m, 1H), 4.85 (d, 2H), 4.64 (d, 1H), 4.52(d, 1H), 4.39(d, 1H), 4.28 (d, 1H), 4.02 (d, 1H), 3.64 (br s, 1H), 2.58 (br s, 1H), 2.42 (s, 3H), 2.40–2.26 (m, 2H), 2.04(s, 3H), 1.56(s,3H), 1.38(s,3H), 1.22(s,3H), 1.13(s,3H), 0.99(s, 3H).

EXAMPLE 6

Preparation of 1,14-benzylidene-7,10-dimethyl diacetonido baccatin III of the formula 16

A mixture of 20 mg of 7,10-acetonide of the formula 13 and 0.1 ml of benzaldehyde was dissolved in 5 ml of toluene and heated to 90° C. in the presence of a crystal of pyridinium p-toluenesulfonate until most of the starting material was consumed as monitored by tlc. Reaction was quenched with a drop of pyridine and concentrated to dryness. The residue was chromatograghed over silica gel using hexane-ethyl acetate as eluent to afford 12 mg of 1,14-benzylidene-7,10-dimethyl diacetonido baccatin III of the formula 16 having dissimilar diacetonides.

EXAMPLE 7

Preparation of 7,10-dimethyl acetonido-14-hydroxy taxol of the formula 23

A mixture of 50 mg of dimethyl diacetonide of the formula 11 and an oxazolidine acid of the formula 8a (42 mg ,1.5equiv.) dissolved in 10 ml of toluene was heated to 90° C. in the presence of dipyridylcarbonate (67 mg) and 4-dimethylaminopyridine (28 mg) under $N_2$ atmosphere. The reaction mixture was diluted with water and extracted with ethyl acetate. The organic extract was washed with water, brine and dried. Removal of solvent gave a residue which was purified over silica gel column using hexane-ethyl acetate as eluent to get 50 mg of the C-13 ester of the formula 19 as a white solid. mp: 170°–172 °C.; $[\alpha]_D$ at 29° C. +35.22 (c 0.205, CHCl$_3$); IR: 1731, 1650, 1380, 1244, 1059, 711 cm$^{-1}$; $^1$H NMR (CDCl$_3$, 200 MHz): δ 8.08(d, J=7.2 Hz,2H), 7.62–7.39(m, 3H), 7.19–6.91(m, 10H), 6.19 (s, 1H), 6.17(d, J=7 Hz, 1H), 5.26(d, J=7 Hz, 1H), 5.24(s, 1H), 4.87(br s, 1H), 4.70(t, J=7 Hz, 1H), 4.66(d, J=6.6 Hz, 1H), 4.23(d, J=8 Hz, 1H), 4.09(d, J=5 Hz, 1H), 3.92(br s, 1H), 3.89(d, J=4.5 Hz, 1H), 2.39–2.19(m, 2H), 2.00(s, 3H), 1.93(s, 3H), 1.66(s, 6H), 1.60(s, 3H), 1.56(s, 6H), 1.51(s, 3H), 1.38(s, 3H), 1.32(s, 3H), 1.21 (s, 3H); FABMS: 948.4232 [M+N]$^+$; 970.4003 [M+Na]$^+$.

The oxazolidine ester of the formula 19 (20 mg), as obtained above was dissolved in 0. 5 ml of trifluoroacetic acid and stirred under $N_2$ atmosphere for 2 h. Excess acid was removed under vacuum and the residue was extracted with ethyl acetate. The organic extract was washed with saturated sodium bicarbonate solution, brine and dried. Concentration of the solvent produced 7,10-dimethyl acetonido-14-hydroxy taxol of the formula 23. mp: 135° C. $[\alpha]_D$ at 28° C. -13.50 (c 0.2, CHCl$_3$); IR: 3444, 1725, 1378, 1254, 1064, 715 cm$^{-1}$; $^1$H NMR(CDCl$_3$, 200 MHz): δ 8.16 (d, J=7.6 Hz, 2H), 7.71 (d, J=7 Hz, 2H), 7.62–7.26 (m,11H), 7.09 (d, J=8.8 Hz, 1H), 5.88 (d, J=8.6 Hz, 1H), 5.44 (s,1H), 5.0–4.85 (m,2H), 4.49 (d, J=8.4 Hz, 1H), 4.47 (s, 1H), 4.38 (d, J=5 Hz,1H), 4.31 (d, J=8.6 Hz, 1H), 4.12 (s,1H), 3.98 (d, J=7 Hz, 1H), 3.69 (br s,1H), 3.63 (br s, 1H), 2.65 (s,3H), 2.48–2.21 (m, 2H), 1.76 (s,3H), 1.68 (s,3H), 1.24 (s,3H), 1.20 (s,3H), 1.04 (s,3H).

Alternatively, the above compound of the formula 23 can also be obtained by the reaction of the oxazolidine ester of the formula 19 with formic acid under $N_2$ atmosphere.

EXAMPLE 8

Preparation of 1,14-dihydroxy oxazolidine ester of the formula 21

Reaction of the oxazolidine ester of the formula 19 (20 mg), as prepared in the example 7, was treated with 4 ml of 2% HCl in tetrahydrofuran (1:1) at 25° C. for 3 h. Reaction was quenched with NaHCO$_3$ and extracted with ethyl acetate. The organic layer was washed with water, brine and dried over anhydrous sodium sulphate. Evaporation of the solvent gave 15 mg of 1,14-dihydroxy oxazolidine ester of the formula 21.

EXAMPLE 9

Preparation of 7,10-dimethyl diacetonido taxotere 25

A mixture of dimethyl diacetonide of the formula 11 (50 mg) and oxazolidino acid of the formula 8b (36 mg,1.5eq.) was dissolved in 10 ml of toluene and heated to 90° C. in the presence of dipyridylcarbonate (65 mg) and 4-dimethylaminopyridine(28 mg) until most of the starting material was consumed. After the workup as mentioned in the example 7 and concentration of the solvent, the residue was purified by column chromatography using hexane-ethyl acetate as eluent to get 50 mg of the ester of the formula 20 as a solid. mp: 184°–186° C.: $^1$H NMR(CDCl$_3$, 200 MHz): δ 8.10 (d, J=7.2 Hz, 2H), 7.72–7.28 (m, 13H) 6.41 (br s, 1 1), 6.18 (s, 1H), 6.16 (d, J=5.8 Hz, 1H), 5.44–5.29 (m, 1H), 5.16 (s, 1H), 4.83 (br s, 1H), 4.79–4.62 (m, 2H), 4.22 (d, J=7.2 Hz, 1H), 4.11 (d, J=5 Hz, 1H), 3.95–3.79 (m, 2H), 2.45–1.90 (m,2H), 1.65 (s, 3H), 1.59(s, 3H), 1.48(s, 3H), 1.42(s, 3H), 1.30(s, 3H), 1.19(s, 3H), 1.04(s, 3H), 1.00(br s, 9H), 0.98(s, 3H).

The oxazolidine ester of the formula 20 (25 mg ) was treated with 90% formic acid (1 ml) and stirred at 25° C. for 4 h under $N_2$ atmosphere. Then the reaction mixture was quenched with NaHCO$_3$ and extracted with ethyl acetate. Concentration of the organic layer provided the amino alcohol 24 (15 mg) which was subjected to the next reaction. Treatment of amino alcohol of the formula 24 with ditert-.butyl dicarbonate (0.01 ml) in the presence of saturated sodium bicarbonate solution (1 ml) produced 7,10-dimethylacetonido taxotere of the formula 25 (8 mg), after purification.

EXAMPLE 10

Preparation of N-tert.butoxycarbonyl-1,14-dihydroxy oxazolidine ester 22

The oxazolidine ester of the formula 20 (20 mg) was dissolved in 2 ml of tetrahydrofuran and treated with 2 ml of 5% HCl at 250° C. for 2 h. Then the reaction mixture was quenched with NaHCO$_3$ and extracted with ethyl acetate. Evaporation of the solvent furnished N-tert.butoxycarbonyl-1,14-dihydroxy oxazolidine ester of the formula 22 (15 mg).

EXAMPLE 11

Preparation of 1,14-bis(trichloroethoxycarbonyl)-10-deacetoxy taxol of the formula 27

50 mg of the 1,14-dihydroxy oxazolidine ester of the formula 21, as prepared in the example 8, was treated with 1 ml of pyridine containing 0.1 ml of trichloroethyl chloroformate and stirred at 80° C. At the end, reaction mixture was poured into ice water and extracted with ethyl acetate. The organic layer was washed with water, NaHCO$_3$, brine and dried. Removal of solvent and purification of the residue over silica gel column afforded the ditroc derivative of the formula 26(35 mg) as a solid. mp: 128°–130° C.; IR: 2928, 1763, 1719, 1642, 1265, 1070, 984, 823 cm$^{-1}$; $^1$H NMR (CDCl$_3$, 200 MHz): δ 8.10 (d, J=7.2 Hz, 2H) 7.70–7.41 (m, 3H), 7.19–6.91 (m, 10H), 6.48(s, 1H), 6.29(br s, 1H), 6.16(d, 1H), 5.31 (d, 1H), 4.92–4.63(m, 10H), 4.41(d, 1H), 4.32(s, 1H), 4.30(d, 1H), 4.01(d, 1H), 2.61 (dd, 1H), 2.28(m,1H), 2.10 (s, 3H), 2.05(s, 3H), 1.95(s, 3H), 1.82(s, 3H), 1.78(s, 3H), 1.39(s, 3H), 1.29(s, 3H), 1.22(s, 3H), 0.98(s, 3H).

Treatment of 25 mg of ditroc ester of the formula 26 with 0.5 ml of trifuoroacetic acid at room temperature for 2 h produced 18 mg of taxol derivative of the formula 27, after the work up as described in the example 7. mp: 190° C.; IR: 3434, 1765, 1740 1720, 1660, 1265, 1103, 1070, 956, 821 cm$^{-1}$; $^1$H NMR (CDCl$_3$, 200 MHz): δ 8.16(d, J=7.2 Hz,2H), 7.68(d, J=7.2 Hz, 2H), 7.55–7.30(m, 11H), 7.21(d, J=9.2 Hz, 1H), 6.58(s, 1H), 6.37(br s, 1H), 6.02(s, 1H), 5.99(d, J=7.8

Hz, 1H), 5.30(s, 1H), 5.10(d, J=3.4 Hz, 1H), 4.95(d, J=11Hz, 1H), 4.90–4.54(m, 6H), 4.50(br s, 1H), 4.04(d, J=4.5 Hz, 1H), 3.73(d, J=11.2 hz, 1H), 3.70(br s, 1H), 3.32(d, J=11 Hz, 1H), 2.40–1.90(m, 2H), 2.25(s, 3H), 2. 14(s, 3H), 1.34(s, 3H), 1.20(s, 3H), 1.16(s, 3H).

EXAMPLE 12

Preparation of 14-hydroxy-10-deacetyl taxol 28

25 mg of the ditroc derivative of the formula 27 was reacted with 5 mg of zinc dust suspended in 2 ml of methanolic acetic acid under $N_2$ atmosphere for 2 h. Reaction mixture was diluted with ethyl acetate and filtered. The filtrate was washed with $NaHCO_3$, brine and dried. Evaporation of solvent gave the tetrahydroxy taxol derivative of the formula 28 (15 mg). $[\alpha]_D$ at 24° C.=+20.202 (c 0.297, $CHCl_3$); $^1$H NMR ($CDCl_3$, 200MH): $\delta$ 8.16 (d, J=7.5 Hz, 2H), 7.71(d, J=7.4 Hz, 2H), 7.60–7.24 (m, 11H), 7.14 (d, J=9.5 Hz, 1H), 6.36 (br s, 1H), 6.01 (d, J=4.2 Hz:, 1H), 5.91 (d, J=9.2 Hz:, 1H), 5.59(s, 1H), 5.50(br s, 1H), 5.03(d, J=3 Hz, 1H), 4.78(br s, 1H), 4.28(br s, 1H), 4.12(br s, 1H), 3.99(d, J=4.3 Hz, 1H), 3.72(d, J=11 Hz, 1H), 3.52(br s, 2H), 3.32(d, J=11 Hz, 1H), 3.19(br s, 1H) 2.14(s, 3H), 2.02(s,3H), 2.05–1.85(m,2H), 1.89(s, 6H), 1.15(s, 3H).

EXAMPLE 13

Preparation of 1,14-bis(trichloroethoxycarbonyl)-taxotere of the formula 30

50 mg of 1,14-dihydroxy oxazolidine ester 21b was dissolved in 2 ml of pyridine and heated to 80° C. in the presence of 0.1 ml of trichloroethyl chloroformate. At the end, the reaction mixture was worked up as described in the example 11 and isolated the ditroc ester of the formula 29 (35 mg).

A solution of the ditroc ester of the formula 29 (2mg) in 1 ml of trifluoroacetic acid was stirred at ice temperature for 2 h and quenched with $NaHCO_3$. After the work up as described in the example 7, the residue was treated with 50 mg of $NaHCO_3$ and 0.01 ml of ditert.butyl dicarbonate in 5 ml of ethyl acetate to afford 10 mg of 1,14-bis (trichloroethoxycarbonyl)-taxotere of the formula 30.

EXAMPLE 14

Preparation of 14-hydroxy taxotere of the formula 31

20 mg of ditroc derivative of the formula 30 was reacted with 5 mg of zinc dust and 0.2 ml of acetic acid dissolved in 0.5 ml of methanol at 25° C. Reaction mixture was diluted with ethyl acetate and filtered. The filtrate was washed with $NaHCO_3$, brine and dried. Evaporation of solvent gave 10 mg of 14-hydroxy taxotere of the formula 31.

EXAMPLE 15

25 mg of 7-10-dimethylacetonido taxol derivative of the formula 23 was reacted with 0.1 ml of benzaldehyde dimethylacetal dissolved in 5 ml of chloroform in the presence of a crystal of p-toluenesulphonic acid for 30 min. Reaction mixture was quenched with pyridine and diluted with chloroform. The organic layer was washed with 5% sodium bicarbonate solution, brine and dried over anhydrous sodium sulfate. Concentration of the solvent and purification of the residue over a silica gel column afforded 15 mg of dissimilar diacetonide ester of the formula 32.

EXAMPLE 16

Preparation of 1,14,7,10-dimethyldiacetonido taxol ester of the formula 33

25 mg of 7,10-dimethyl acetonido taxol derivative of the formula 23 was treated with 2,2-dimethoxypropane and a crystal of pyridinium p-toluenesulphonate dissolved in 5 ml of chloroform at 40° C. for 30 min. The reaction was quenched with $NaHCO_3$ and extracted with ethyl acetate. Concentration of the organic layer provided 20 mg of dimethyldiacetonido ester of the formula 33; IR: 3436, 1724, 1665, 1513, 1269, 1102, 980, 557 cm$^{-1}$; $^1$ H NMR ($CDCl_3$, 200 Hz: $\delta$ 8.12(d, J=7.4 Hz, 2H), 7.81 (d, J=6.6 Hz, 2H), 7.69–7.32(m, 11H), 7.28(d, J=7 Hz, 1H), 6.20(d, J=5.3 Hz, 1H), 6.19(br s, 1H), 5.89(dd, J=9, 2.8 Hz, 1H), 5.18(s, 1H), 4.93(d, J=17 Hz, 2H), 4.68(t, J=7 Hz, 1H), 4.34(d, J=7.5 Hz, 1H), 4.18(br s, 1H), 4.16(d, J=4.6 Hz, 1H), 4.01(d, J=7.5 Hz, 1H), 3.92(d, J=5 Hz, 1H), 2.44(s, 3H), 2.39–1.98(m, 2H), 1.67(s.3H), 1.58(s, 3H), 1.57(s, 3H), 1.49(s, 3H), 1.31(s, 3H), 1.27 (s, 3H), 1.20 (s, 3H), 1.13(s, 3H).

EXAMPLE 17

Preparation of 7,10-dimethylacetonido-10-deacetoxy pseudo taxol of the formula 35

A mixture of 7,10-acetonide of the formula 13 (50 mg) and an oxazolidine acid of the formula 8a (40 mg) was dissolved in 10 ml of toluene and stirred in the presence of dipyridylcarbonate (70 mg) and 4-dimethylaminopyridine (30 mg) at 80° C. until the starting material was consumed as monitored by tlc. Toluene was evaporated and the residue was extracted with ethyl acetate. The organic extract was washed with water, brine and dried. Concentration of the solvent and purification of the gummy mass by silica gel column afforded 45 mg of C-14 oxazolidine ester of the formula 34 as a solid.; $^1$ H NMR ($CDCl_3$, 200 Hz): $\delta$ 8.07(d, J=7 Hz, 2H), 7.71–7.45(m, 3H), 7.28–6.90(m, 10H), 6.94(s, 1H), 6.20(d, J=3.3 Hz, 1H), 6.08(d, J=7 Hz, 1H), 5.52(d, J=5 Hz, 1H), 5.26(d, J=7 Hz, 1H), 4.91–4.82 (m, 1H), 4.64(d, J=7 Hz, 1H), 4.52(d, J=11.6 Hz, 1H), 4.44(d, J=8.7 Hz, 1H), 4.24 (d, J=9 Hz,1H), 4.19(d, J=5 Hz, 1H), 3.87(d, J=7 Hz, 1H), 3.75–3–62(m, 1H), 2.45–2.24(m, 2H), 2.02(s, 3H), 1.92(s, 3H), 1.89(s, 3H), 1.80(s, 3H) 1.63(s, 3H), 1.36(s, 3H), 1.27(s, 3H), 1.04(s, 3H), 0.86(s, 3H).

A solution of the above C-14 ester of the formula 34 (25 mg) in 1 ml of trifluoroacetic acid was stirred at 25° C. for 2 h. Excess acid was removed and extracted with ethyl acetate. Ethyl acetate extract was washed with water, NaHCO3, brine and dried. Evaporation of solvent furnished the pseudo taxol derivative of the formula 35 (15 mg).

EXAMPLE 18

Preparation of 7, 10-acetonido pseudo taxotere of the formula 37

A mixture of 7,10-acetonide of the formula 11 (50 mg) and an oxazolidine acid of the formula 8c (50 mg) was heated to 80° C. in the presence of didipyridylcarbonate (70 mg) and 4-dimethylaminopyridine (30 mg) dissolved in 10 ml of toluene until the starting material was consumed. Toluene was evaporated and the residue was extracted with ethyl acetate. The organic extract was washed with water, brine and dried. Concentration of the solvent and purification of the gummy mass by column chromatography afforded the C-14 oxaxolidine ester of the formula 36 (45 mg) as a solid.; $^1$H NMR ($CDCl_3$, 200 Hz): $\delta$ 8.12(d, J=7 Hz, 2H), 7.72–7.46(m, 3H), 7.43–7.22(m, 10H), 6.90(s, 1H), 6.19(d, J=3.6 Hz, 1H), 6.11(d, J=7 Hz, 1H), 5.32(br s, 1H), 5.05(br s, 1H), 4.91–4.78(m, 1H), 4.64(d, J=5.4 Hz, 1H), 4.52(d, J=7.3 Hz, 1H), 4.40(d, J=8.7 Hz, 1H), 4.26(d, J=5 Hz, lN), 4.24(br s, 1H), 3.87(d, J=7 Hz, 1H), 3.75–3.61(m, 1H), 2.42–2.18(m, 2H), 1.83(s, 3H), 1.80(s, 3H), 1.78(s, 3H), 1.72(s, 3H), 1.70(s, 3H), 1.62(s, 3H), 1.39(s, 3H), 1.17(br s, 9H), 1.08(s, 3H), 1.03(s, 3H).

The C-14 oxazolidine ester of the formula 36 (25 mg) was dissolved in 1 ml of 90% formic acid and stirred at 25° C. for 2 h. Excess acid was removed by vacuum and the residue was extracted with ethyl acetate. Concentration of the solvent produced 10 mg of pseudo taxotere derivative of the formula 37.

EXAMPLE 19

Preparation of the vinyl compound of the formula 17a where $R^9 = R^{10} = Me$, $R = Ph$ A mixture of the hydroxy compound of the formula 18a where R=Ph (1.5 g) and 2,2-dimethoxypropane (11 ml) was dissolved in 15 ml of toluene and heated to 90° C. in the presence of a crystal of pyridinium p-toluenesulfonate until the starting material was disappeared as monitored by tlc. Reaction was quenched with a drop of pyridine and concentrated to dryness. The residue was purified by column chromatography using hexane-ethyl acetate as eluent to obtain 1.25 g of the above mentioned vinyl derivative of the formula 17a.

EXAMPLE 20

Preparation of the oxazolidine acid of the formula 8a

To a mixture of a vinyl compound of the formula 17a (600 mg) and sodium bicarbonate (1.13 g) suspended in a solvent mixture containing carbon tetrachloride (5.8 ml), acetonitrile (5.8 ml) and water (8.6 ml), sodium periodate (2.37 g) was added and stirred at 25° C. for 15 min. To it, ruthenium chloride (65 mg) was added slowly and continued stirring for 48 h. Reaction mixture was poured into water and extracted with ether. The aqueous layer was carefully acidified with dilute HCl and extracted with chloroform. The organic extract was washed with water, brine and dried. Concentration of the solvent afforded 530 mg of the acid of the formula 8a as a solid.

EXAMPLE 21

Preparation of the vinyl compound of the formula 17b where $R^9 = R^{10} = Me$, $R = OBu^t$ A mixture of the hydroxy compound of the formula 18b where R=OBu$^t$ (1.0 g) and 2,2-dimethoxypropane (8 ml) was dissolved in 15 ml of toluene and heated to 90° C. in the presence of a crystal of pyridinium p-toluenesulfonate until the starting material was disappeared as monitored by tlc. Reaction was quenched with a drop of pyridine and concentrated to dryness. The residue was purified by column chromatography using hexane-ethyl acetate as eluent to obtain 750 mg of the above mentioned vinyl derivative of the formula 17b.

EXAMPLE 22

Preparation of the oxazolidine acid of the formula 8b

To a mixture of a vinyl compound of the formula 17b,(500 mg) and sodium bicarbonate (1.13 g) suspended in a solvent mixture containing carbon tetrachloride (5.8 ml), acetonitrile (5.8 ml) and water (8.6 ml), sodium periodate (2.25 g) was added and, stirred at 25° C. for 15 min. To it, ruthenium chloride (60 mg) was added slowly and continued stirring for 48 h. Reaction mixture was poured into water and extracted with ether. The aqueous layer was carefully acidified with dilute HCl and extracted with chloroform. The organic extract was washed with water, brine and dried. Concentration of the solvent afforded 410 mg of the acid of the formula 8b as a gummy solid.

EXAMPLE 23

IN VITRO ANTI-CANCER ACTIVITY DATA OF 7,10-DIMETHYLACETONIDO 14-HYDROXY TAXOL (Compound 23) ON LEUKEMIA, OVARIAN AND BREAST CANCER CELL LINES IN COMPARISON TO TAXOL All the values are given in μm concentrations:

| | LEUKEMIA GI50 VALUES | | | | |
|---|---|---|---|---|---|
| cell line | SR | HL60 | K-562 | Molt-4 | RPMI-8226 |
| compd 23 | 0.084 | 0.044 | 0.247 | 0.267 | 0.057 |
| Taxol | 0.033 | 0.01 | 0.015 | 0.053 | 0.006 |

| | COLON CANCER GI50 | | | | |
|---|---|---|---|---|---|
| cell line | HCT 116 | HCT 15 | HT-29 | KM12 | SW 620 |
| compd 23 | 0.228 | 2.14 | 0.079 | 0.077 | 0.131 |
| Taxol | 0.019 | 0.57 | 0.008 | 0.016 | 0.02 |

| | OVARIAN CANCER GI50 | | | |
|---|---|---|---|---|
| cell line | IGR-OV1 | OVCAR3 | OVCAR4 | OVCAR5 |
| compd 23 | 0.066 | 0.131 | 1.86 | 0.77 |
| Taxol | 0.028 | 0.022 | 0.38 | 0.075 |

| | BREAST CANCER GI50 | | | | | | |
|---|---|---|---|---|---|---|---|
| cell line | MCF7 | MDA-MB 231 | H5578T | MDA-MB 435 | BT 549 | MDA-N | T47D |
| compd 23 | 0.07 | 0.50 | 0.137 | 0.03 | 0.443 | 0.033 | 0.158 |
| Taxol | 0.009 | 0.1 | 0.012 | 0.006 | 0.06 | 0.004 | 0.109 |

| compd | TGI values: | | | | | | |
|---|---|---|---|---|---|---|---|
| compd 23 | >30 | >30 | 0.89 | 0.12 | 11.2 | 0.12 | 17.7 |
| Taxol | 1.0 | 0.67 | 0.15 | 0.025 | 0.7 | 0.015 | 1.0 |

The notations GI50, TGI refer to the concentrations of the agent in the assay that produced 50% growth inhibition, total growth inhibition respectively.

We claim:

1. A compound of formula 1

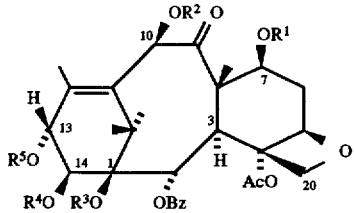

wherein R⁵ is selected from hydrogen, lower alkyl, unsubstituted or substituted phenyl, tri(alkyl or phenyl) silyl, lower alkanoyl, substituted alkanoyl or amino alkanoyl or a group having the formula 3

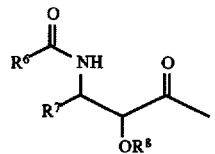

in which R⁶ is selected from hydrogen, lower alkyl, unsubstituted or substituted phenyl, lower alkoxy, substituted alkoxy, phenoxy, substituted phenoxy, amino or substituted amino, R⁷ is selected from hydrogen, lower alkyl, unsubstituted or substituted phenyl, hydroxy alkyl, alkoxy alkyl or aminoalkyl and R⁸ is selected from hydrogen, lower alkyl, lower alkanoyl, substituted alkanoyl, or amino alkanoyl; OR¹ and OR² are taken together to form a cyclic ring of formula 4

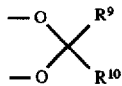

where R⁹ and R¹⁰ are selected independently from hydrogen, lower alkyl, phenyl, or substituted phenyl, lower alkoxy, amino or substituted amino or R⁹ and R¹⁰ are taken together as a single atom wherein the atom is oxygen or sulfur; R³ and R⁴ are selected independently from hydrogen, lower alkyl, lower alkanoyl, or substituted lower alkanoyl or OR³ and OR⁴ are taken together to form a cyclic ring of formula 4

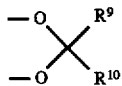

where R⁹ and R¹⁰ are selected independently from hydrogen, lower alkyl, phenyl, or substituted phenyl, lower alkoxy, amino or substituted amino or R⁹ and R¹⁰ taken together are a single atom, wherein the atom is oxygen or sulfur.

2. A compound of the formula 1, as defined in claim 1, wherein R⁵ is a group represented by

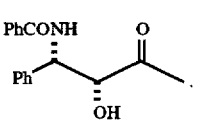

3. A compound of the formula 1, as defined in claim 1, wherein R⁵ is a group represented by

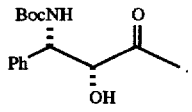

4. A compound of the formula 7, according to claim 1,

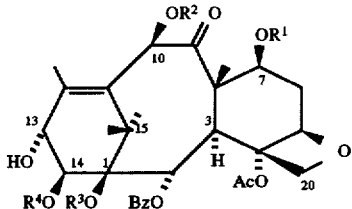

wherein R¹, R² together and R³, R⁴ independently have the meaning as described in claim 1 or both R¹, R² together and R³, R⁴ together form cyclic rings leaving a free hydroxyl group at C-13 position.

5. A compound of the formula 9,

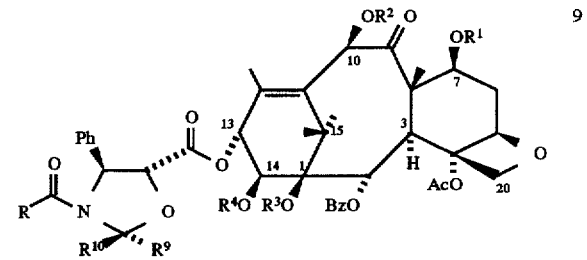

wherein R, R¹, R², R³, R⁹, and R¹⁰ have the meaning given in claim 1.

6. A compound of the formula 10,

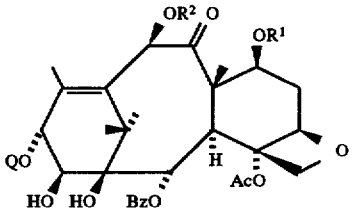

wherein Q represents the group having, the formula U or V,

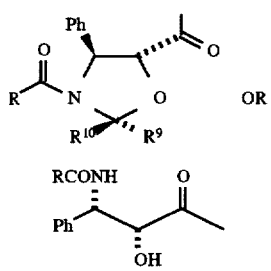

and R, R¹, R², R⁹ and R¹⁰ have the meaning given in claim 1.

7. A compound having the formula T,

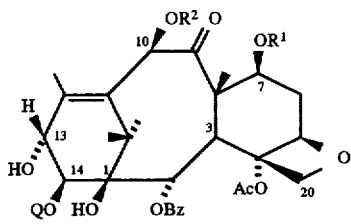

where Q represents the group having the formula U or V

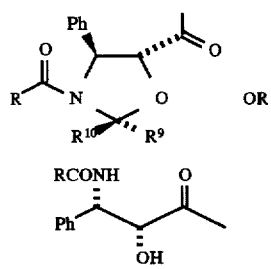

and R, R¹, R², R⁹ and R¹⁰ have the meaning given in claim 1.

8. A compound of the formula 1 as defined in claim 1, wherein R⁵ is,

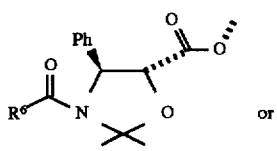

a group of formula 3,

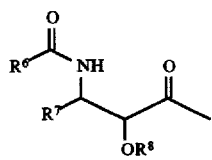

where R⁶ is phenyl or tert.butoxycarbonyl, R⁷ is phenyl and R⁸ is hydrogen, wherein OR¹ and OR² are taken together to form a cyclic ring of formula 4,

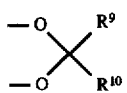

where R⁹ and R¹⁰ are methyl, R³ is hydrogen or COOCH₂CCl₃; R⁴ is hydrogen or COOCH₂CCl₃; or OR³ and OR⁴ taken together form a cyclic ring of formula 4 where R⁹ is phenyl or methyl and R¹⁰ is hydrogen or methyl.

9. A pharmaceutical composition comprising compounds of the formula 1 as defined in claim 1, a derivative thereof or a pharmaceutical salt thereof and a pharmaceutically acceptable non-toxic excipient, diluent or carrier.

10. A method of treating cancer or a virus comprising administering an effective amount of composition of formula 1.

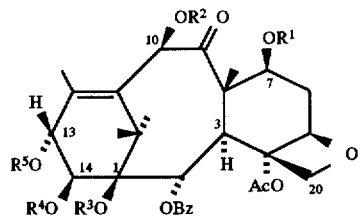

wherein R⁵ is selected from hydrogen, lower alkyl, unsubstituted or substituted phenyl, tri(alkyl or phenyl) silyl, lower alkanoyl, substituted alkanoyl or amino alkanoyl or a group having the formula 3.

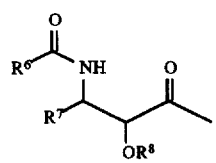

in which R⁶ is selected from hydrogen, lower alkyl unsubstituted or substituted phenyl, lower alkoxy, substituted alkoxy, phenoxy, substituted phenoxy, amino or substituted amino; R⁷ is selected from hydrogen, lower alkyl, unsubstituted or substituted phenyl, hydroxy alkyl, alkoxy alkyl or aminoalkyl and R⁸ is selected from hydrogen, lower alkyl, lower alkanoyl, substituted alkanoyl or amino alkanoyl; OR¹ and OR² are taken together to form a cyclic ring having the formula 4,

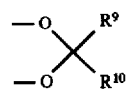

where R⁹ and R¹⁰ are selected independently from hydrogen, lower alkyl, phenyl or substituted phenyl, lower alkoxy, amino, substituted amino or R⁹ and R¹⁰ are taken together as a single atom, wherein the atom is oxygen or sulfur; R³ and R⁴ are selected independently from hydrogen, lower alkyl, lower alkanoyl, or substituted lower alkanoyl or OR³ and OR⁴ when taken together to form a cyclic ring having the formula 4,

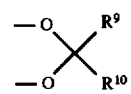

where R⁹ and R¹⁰ are selected independently from hydrogen, lower alkyl, phenyl or substituted phenyl, lower alkoxy, amino or substituted amino or R⁹ and R¹⁰ are taken together as a single atom, wherein the atom is oxygen or sulfur.

* * * * *